United States Patent [19]

Dennis et al.

[11] Patent Number: 4,496,768

[45] Date of Patent: Jan. 29, 1985

[54] PROCESS FOR THE PRODUCTION OF ALDEHYDES BY HYDROFORMYLATION OF ALPHA-OLEFINS

[75] Inventors: Alan J. Dennis, Middlesbrough; George E. Harrison, Billericay; James P. Wyber, Stockton-on-Tees, all of England

[73] Assignee: Davy McKee Limited, London, England

[21] Appl. No.: 501,859

[22] Filed: Jun. 7, 1983

[30] Foreign Application Priority Data

Nov. 6, 1982 [GB] United Kingdom ............... 8217037

[51] Int. Cl.$^3$ ............................................. C07C 45/50
[52] U.S. Cl. ........................................ 568/454; 568/909
[58] Field of Search .................... 568/454, 882, 909

[56] References Cited

U.S. PATENT DOCUMENTS

| | | | |
|---|---|---|---|
| 3,239,569 | 3/1966 | Slaugh et al. | 568/454 |
| 3,499,933 | 9/1970 | Pruett et al. | 568/454 |
| 3,527,809 | 4/1979 | Paul et al. | 568/454 |
| 3,547,964 | 3/1970 | Pruett et al. | 260/429 R |
| 3,560,539 | 12/1970 | Olivier et al. | 260/429 R |
| 3,641,076 | 2/1971 | Booth | 260/429 R |
| 3,644,446 | 2/1971 | Booth | 260/429 R |
| 3,725,483 | 4/1973 | Deffner et al. | 568/454 |
| 3,733,361 | 5/1973 | Deffner et al. | 568/454 |
| 3,859,359 | 2/1972 | Booth et al. | 568/454 |
| 3,907,847 | 9/1975 | Keblys | 260/429 R |
| 3,917,661 | 11/1975 | Pruett et al. | 568/454 |
| 3,933,919 | 1/1976 | Wilkinson | 568/454 |
| 3,956,177 | 5/1976 | Zuech | 568/454 |
| 4,096,192 | 6/1978 | Bhatia et al. | 568/454 |
| 4,101,588 | 7/1978 | Nienburg et al. | 568/454 |
| 4,107,079 | 8/1978 | Chevallier et al. | 252/429 |
| 4,108,905 | 8/1978 | Wilkinson | 568/454 |
| 4,135,911 | 1/1979 | Balmat | 423/22 |
| 4,158,020 | 6/1979 | Stautzenberger et al. | 568/454 |
| 4,158,042 | 3/1980 | Zuech | 568/454 |
| 4,200,591 | 4/1980 | Hignett et al. | 568/454 |
| 4,200,592 | 4/1980 | Hignett et al. | 568/454 |
| 4,224,255 | 9/1980 | Smith | 568/451 |
| 4,258,215 | 3/1981 | Dawes | 568/454 |
| 4,262,142 | 4/1981 | Sherman et al. | 568/454 |
| 4,267,383 | 5/1981 | Booth | 568/454 |
| 4,306,087 | 12/1981 | Matsumoto | 568/454 |

FOREIGN PATENT DOCUMENTS

| | | | |
|---|---|---|---|
| 0003753 | 1/1979 | European Pat. Off. | 568/454 |
| 0028892 | 10/1980 | European Pat. Off. | 568/454 |
| 40326 | 5/1973 | Japan | 568/454 |
| 10765 | 5/1979 | Japan | 568/454 |
| WO80/00081 | 1/1980 | PCT Int'l Appl. | 568/454 |
| 988941 | 6/1961 | United Kingdom | 568/454 |
| 995459 | 8/1962 | United Kingdom | 568/454 |
| 1243189 | 12/1967 | United Kingdom | 568/454 |
| 1243190 | 12/1967 | United Kingdom | 568/454 |
| 1207561 | 1/1968 | United Kingdom | 568/454 |
| 1228201 | 4/1968 | United Kingdom | 568/454 |
| 1338225 | 12/1969 | United Kingdom | 568/454 |
| 1198815 | 7/1970 | United Kingdom | 568/454 |
| 1198816 | 7/1970 | United Kingdom | 568/454 |
| 1325199 | 8/1970 | United Kingdom | 568/454 |
| 1338237 | 12/1970 | United Kingdom | 568/454 |
| 1448090 | 11/1973 | United Kingdom | 568/454 |
| 1455645 | 4/1974 | United Kingdom | 568/454 |
| 1460870 | 7/1975 | United Kingdom | 568/454 |
| 1461900 | 7/1975 | United Kingdom | 568/454 |
| 1462342 | 7/1975 | United Kingdom | 568/852 |
| 1463947 | 10/1975 | United Kingdom | 568/454 |
| 1557396 | 3/1977 | United Kingdom | 568/852 |
| 1582010 | 4/1977 | United Kingdom | 568/454 |
| 1586805 | 9/1977 | United Kingdom | 568/852 |
| 2000124 | 5/1978 | United Kingdom | 568/454 |
| 2068377 | 2/1981 | United Kingdom | 568/454 |

OTHER PUBLICATIONS

Low Pressure Oxo Process Yields a Better Product Mix, Chemical Engineering, Dec. 5, 1977, pp. 110–115.

*Primary Examiner*—Werren B. Lone
*Attorney, Agent, or Firm*—Bernard, Rothwell & Brown

[57] ABSTRACT

A continuous process for the production an aldehyde by hydroformylation of an optionally substituted alpha-olefin comprises:
  providing a hydroformylation zone containing a charge of a liquid reaction medium having dissolved therein a complex rhodium hydroformylation catalyst comprising rhodium in complex combination with carbon monoxide and with a cyclic phosphite having a bridgehead phosphorus atom linked to three oxygen atoms at least two of which form together with the bridgehead phosphorus atom part of a ring;
  supplying said alpha-olefin to the hydroformylation zone;
  maintaining temperature and pressure conditions in the hydroformylation zone conducive to hydroformylation of the alpha-olefin;
  supplying make-up hydrogen and carbon monoxide to the hydroformylation zone; and
  recovering from the liquid hydroformylation medium a hydroformylation product comprising at least one aldehyde.

15 Claims, No Drawings

PROCESS FOR THE PRODUCTION OF ALDEHYDES BY HYDROFORMYLATION OF ALPHA-OLEFINS

This invention relates to a hydroformylation process, particularly a process for the hydroformylation of alpha-olefins to give aldehydes.

Hydroformylation is a well known reaction in which an olefin (usually a terminal olefin) is reacted under suitable temperature and pressure conditions with hydrogen and carbon monoxide in the presence of a hydroformylation catalyst to give an aldehyde, or a mixture of aldehydes, having one more carbon atom than the starting olefin. Thus ethylene yields propionaldehyde, whilst propylene yield a mixture of n- and iso-butyraldehydes, of which the straight chain-n-isomer is usually the more commercially desirable material. In some cases the catalyst can be modified so that the products are not aldehydes but are the corresponding alcohols.

The catalysts first used in this reaction were cobalt-containing catalysts, such as cobalt octacarbonyl. The use of such catalysts necessitates exceptionally high operating pressures, e.g. several hundred bars, in order to maintain the catalysts in their active form. The n-/isomolar ratio of the aldehyde products is not particularly high, e.g. about 3:1 or 4:1, and product recovery is generally complicated because the cobalt carbonyl catalysts are volatile and chemically unstable in the absence of high hydrogen and carbon monoxide partial pressures.

Modified forms of cobalt carbonyls have also been described in the literature as hydroformylation catalysts. For example, British Patent Specification No. 988,941 proposes the use as hydroformylation catalyst of a cobalt complex containing at least one biphyllic ligand containing trivalent phosphorus, the three valencies of the phosphorus atom being satisfied with any organic group and the organic group optionally satisfying two of the phosphorus valencies to form a heterocyclic compound. Such complexes yield, however, alcohols rather than aldehydes as the major hydroformylation product.

British Patent Specification Nos. 1,198,815 and 1,198,816 describe the production and use as hydroformylation catalysts in batch reactions of complexes of cobalt carbonyl and various cyclic phosphorus compounds, including 4-hydro-2,6,7-trioxa-1-phosphabicyclo-[2,2,2]-octane and substituted derivatives thereof. Such complexes are ascribed (see page 25, lines 54 to 63 of British Patent Specification No. 1,198,815) the structural formula:

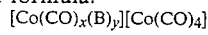

[Co(CO)$_x$(B)$_y$][Co(CO)$_4$]

in which B is the cyclic phosphorus compound, x and y are whole numbers from one to 4 and x+y=5, and are said to be more thermally stable than cobalt carbonyls. However, their thermal stability is clearly still far from acceptable since it is recommended to employ them, in order to render them even more thermally stable, in admixture with a trialkylamine having a pKa acidity of at least +8 but not greater than +15, e.g. trimethylamine, tri-n-butylamine, and the like. Operating temperatures of 93° C. to 246° C. are used, while the pressure can be from 35 to 350 kg/cm² gauge (from about 35.3 to about 344 bar), preferably from 70 to 210 kg/cm² gauge (from about 69.7 to about 207 bar). n-/iso-ratios in the range of from about 4:1 to about 8:1 are said to be obtainable. It is a disadvantage of this process that significant amounts of alcohol rather than aldehyde are produced. Thus in the hydroformylation product, from 5% up to about 25% by weight consists of the alcohol, the balance being the aldehyde (see page 25, lines 97 to 102 of British Patent Specification No. 1198815). Moreover the catalyst activity is not very high, contact times of at least 30 minutes being recommended. It is also a feature of the process that polymeric byproducts are formed. This is perhaps a consequence of using aliphatic triamines as additives since these compounds and other basic substances are known to catalyse the self-condensation reactions of aldehydes.

More recently there have been proposed rhodium complex hydroformylation catalysts for hydroformylation of alpha-olefins, that is to say compounds containing the group —CH=CH$_2$ or >C=CH$_2$. These catalysts generally comprise rhodium in complex combination with carbon monoxide and with a ligand, such as triphenylphosphine and are used in conjunction with excess ligand. Such rhodium complex catalysts are now in use in numerous hydroformylation plants throughout the world and many plants formerly operating with cobalt catalysts have been, or are being, converted for operation with these newer rhodium catalysts. Such catalysts have the advantage not only of lower operating pressures e.g. about 20 kg/cm² absolute (19.6 bar) or less, but also of being capable of yielding high n-/iso-aldehyde product ratios from alpha-olefins; in many cases n-/iso-aldehyde molar ratios of 10:1 and higher can be achieved. Moreover, since the catalyst is non-volatile, product recovery is greatly simplified. A fuller description of the process will be found in the article "Low-pressure OXO process yields a better product mix", Chemical Engineering, Dec. 5, 1977, pages 110 to 115. Also extremely relevant to this process are U.S. Pat. No. 3,527,809 and British Patent Specification Nos. 1,338,237 and 1,582,010. The production of n-valeraldehyde by rhodium-catalysed hydroformylation of butene-1 is taught in particular by European Patent Publications No. 00 16 285 and 00 16 286.

The rhodium catalyst adopted in commercial practice comprises rhodium in complex combination with carbon monoxide and with triphenylphosphine. Although the nature of the catalytic species is not entirely clear, it has been postulated to the HRh(CO)(PPh$_3$)$_3$ (see, for example, page 792 of "Advanced Inorganic Chemistry" (Third Edition) by F. Albert Cotton and Geoffrey Wilkinson, published by Interscience Publishers). The reaction solution contains excess triphenylphosphine and operating temperatures in the range of from about 90° C. to about 120° C. are recommended.

U.S. Pat. No. 3,527,809 also proposes the use of various other ligands, including phosphites, such as triphenylphosphite, in place of triphenylphosphine. Although the use of triphenylphosphite has the advantage that lower operating temperatures can be used, we have found that the catalyst tends to deactivate moderately rapidly, a phenomenon that is accompanied by disappearance of free triphenylphosphite ligand and by an increase in the rate of formation of "heavy" materials (i.e. high boiling byproducts). Further teaching as to the use of phosphites in hydroformylation of terminal olefins will be found in U.S. Pat. Nos. 3,917,661, 3,499,933 and 4,262,142. There are numerous other references in the literature to the use of phosphite ligands in homogeneous rhodium complex hydroformylation catalysts.

Examples include U.S. Pat. Nos. 3,547,964, 3,560,539, 3,641,076, 3,644,446, 3,859,359, 3,907,847, 3,933,919, 3,956,177, 4,096,192, 4,101,588, 4,108,905, 4,135,911, 4,158,020, 4,195,042, 4,200,591, 4,200,592, 4,224,255 and 4,267,383, as well as British Patent Specification Nos. 995,459, 1,207,561, 1,228,201, 1,243,189, 1,243,190, 1,263,720, 1,338,225, 1,448,090, 1,455,645, 1,460,870, 1,461,900, 1,462,342, 1,463,947, 1,557,396, 1,586,805, 2000124A and 2068377A, European Patent Publication Nos. 0003753 and 0028892, and International Patent Publication No. WO 80/00081.

Other examples include Japanese Patent Publication Nos. 10765/69 published 19th May 1969 and 40326/73 published 30th Nov. 1973.

U.S. Pat. No. 4,107,079 describes solid insoluble metallic complexes for use as hydroformylation catalysts which may contain rhodium and a ligand. Amongst ligands suggested are phosphites, including the phosphite of trimethylol propane (column 3 line 61).

Example 2 of British Patent Specification No. 1,325,199 teaches the use, in a batch reaction for the hydroformylation of hexene-1, of the catalyst [RhCl(CO)(tmpP)$_2$] where tmp represents the radical

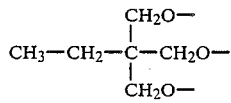

Reaction is effected in the liquid phase using a 50% v/v solution of hexene-1 in benzene. At 100° C. 57 mol% conversion of hexene-1 is said to be achieved in 6 hours under partial pressures of carbon monoxide and hydrogen of 12 atmospheres (about 12 bar) to give a reported yield of aldehydes (based on hexene-1 converted) of 100%, of which 65 mole% is 1-heptanal. According to page 2, lines 55 to 61, catalysts devoid of chlorine are as efficient as those containing it. Conversions of only 57% in 6 hours are not commercially interesting. Although it will in many cases be desirable to obtain the highest possible n-/iso-aldehyde ratio from an alpha-olefin because the n-isomer is usually the more commercially valuable product, particularly when a new plant is brought into operation, there may be occasions when a high n-/iso-ratio may not be so desirable. For example, operators of existing hydroformylation plants using cobalt-based catalysts may wish to take advantage of the lower operating costs afforded by rhodium complex hydroformylation catalysts, whilst not necessarily wanting to obtain a different aldehyde isomer ratio from that they obtained previously with the cobalt catalysts, since they already have a market for the iso-aldehyde as well as for the n-aldehyde. In this event, although it is possible to operate the rhodium/triphenylphosphine catalysed process under conditions producing, for example, an n-/iso-aldehyde ratio of 4:1 (instead of the 10:1 or better obtainable under optimum conditions), the operating conditions must be selected so as to be far from optimum so that operating costs are increased, whilst the risk of catalyst deactivation under these non-optimum conditions is increased significantly.

In all hydroformylation processes there is a possibility of product aldehyde undergoing reduction to the corresponding alcohol. Generally speaking such further reduction is undesirable because not only may this result in a lower yield of the desired aldehyde but also the alcohol can react with the aldehyde product to give high boiling hemi- and di-acetals.

There is accordingly a need to provide a process for the production of aldehydes from alpha-olefins which is capable of yielding an aldehyde product mixture having an n-/iso-ratio approximating to that obtainable using cobalt hydroformylation catalysts, whilst enabling the plant operator to benefit from the lower operating pressures and temperatures afforded by use of rhodium complex catalysts.

Accordingly the present invention seeks to provide a continuous hydroformylation process for the production of aldehyde mixtures from alpha-olefins, which utilises rhodium complex catalysts under favourable operating conditions and which is capable of yielding an n-/iso-aldehyde ratio approximating to that obtainable with cobalt hydroformylation catalysts. The present invention further seeks to provide a process which is capable of continuous operation for hydroformylation of a wide variety of olefinically unsaturated compounds, containing an alpha-olefinic bond, at commercially acceptable reaction rates, to give the corresponding aldehydes. It further seeks to provide such a process which is characterised by little or negligible catalyst deactivation rates and by low rates of formation of "heavies" (aldehyde condensation by-products). Yet again it seeks to provide a process for rhodium-catalysed hydroformylation of optionally substituted alpha-olefins which utilises a homogeneous rhodium complex catalyst embodying a phosphorus-containing ligand which is capable of operation for extended periods with little or no degradation of the ligand. It is further sought to provide a hydroformylation process in which the amounts of olefin hydrogenation by-products and of aldehyde hydrogenation by-products are very small.

According to the present invention there is provided a continuous hydroformylation process for the production of an aldehyde by hydroformylation of an optionally substituted alpha-olefin which comprises:

providing a hydroformylation zone containing a charge of a liquid reaction medium having dissolved therein a complex rhodium hydroformylation catalyst comprising rhodium in complex combination with carbon monoxide and with a cyclic phosphite ligand having a bridgehead phosphorus atom linked to three oxygen atoms at least two of which form together with the brightened phosphorus atom part of a ring;

supplying said alpha-olefin to the hydroformylation zone;

maintaining temperature and pressure conditions in the hydroformylation zone conducive to hydroformylation of the alpha-olefin;

supplying make-up hydrogen and carbon monoxide to the hydroformylation zone; and recovering from the liquid hydroformylation medium a hydroformylation product comprising at least one aldehyde.

The catalyst used in the process of the present invention is a rhodium carbonyl complex comprising rhdoium in complex combination with carbon monoxide and with a cyclic organic phosphite ligand having a phosphorus atom in a bridgehead position, which phosphorus atom is linked to three oxygen atoms at least two of which form, together with the phosphorus atom to which they are attached, part of a ring. Preferably this catalyst and the reaction medium are substantially halogen-free. Although the structure of such rhodium carbonyl complexes is not entirely clear, it is postulated that the preferred halogen-free complexes may have the structure:

$$RhH_m(CO)_n(L)_p$$

in which m is zero, 1 or 2, n and p are each, independently of the other, an integer of from 1 to about 4, and L is a cyclic phosphite ligand as defined above, provided that the sum of m, n and p is from 4 to 6.

The optionally substituted alpha-olefin contains at least one alpha-olefinic carbon-carbon double bond (or ethylenic bond) and contains at least 2 carbon atoms. Such compounds have the general formula:

$$R_1R_2C=CH_2$$

in which $R_1$ and $R_2$ each represent a hydrogen atom or an organic radical or together represent a divalent radical which, together with the carbon atom to which they are attached, form a non-aromatic carbocyclic or heterocyclic ring. (For convenience hereafter the term "alpha-olefin" is some times used to designate "optionally substituted alpha-olefin"). Preferably such alpha-olefins are halogen-free and sulphur-free. Preferably the olefinically unsaturated compound contains from 2 to about 20 carbon atoms. Illustrative starting olefins include alpha- olefins, e.g. alkenes, arylalkenes, and cycloalkenes, and substituted alpha-olefins, e.g. ethers of unsaturated alcohols, and esters of unsaturated alcohols and/or acids.

As examples of alpha-olefins ther may be mentioned alpha-olefins (e.g. ethylene, propylene, butene-1, iso-butylene, pentene-1, 2-methylbutene-1, hexene-1, heptene-1, octene-1, 2,4,4-trimethylpentene-1, 2-ethylhexene-1, nonene-1, 2-propylhexene-1, decene-1, undecene-1, dodecene-1, octadecene-1, eicosene-1, 3-methylbutene-1, 3-methylpentene-1, 3-ethyl-4-methylpentene-1, 3-ethylhexene-1, 4,4-dimethylnonene-1, 6-propyldecene-1, 1,5-hexadiene, vinyl cyclohexane, allyl cyclohexane, styrene, alpha-methylstyrene, allylbenzene, divinylbenzene, 1,1-diphenylethylene, o-vinyl-p-xylene, p-vinylcumene, m-hexylstyrene, 1-allyl-4-vinylbenzene, beta-vinylnaphthalene, and the like), alpha-alkenols (e.g. allyl alcohol, hex-1-en-4-ol, oct-1-en-4-ol, and the like), alpha-alkenyl ethers (e.g. vinyl methyl ether, vinyl ethyl ether, allyl ether ether, allyl t-butyl ether, allyl phenyl ether, and the like), alpha-alkenyl alkanoates (e.g. vinyl acetate, allyl acetate, and the like), alkyl alpha-alkenoates (e.g. methyl acrylate, ethyl acrylate, n-propyl oct-7-enoate, methyl methacrylate, and the like), alpha-olefinically unsaturated aldehydes and acetals (e.g. acrolein, acrolein dimethyl and diethyl acetals, and the like), alpha-olefinically unsaturated nitriles (e.g. acrylonitrile and the like), and alpha-olefinically unsaturated ketones (e.g. vinyl ethyl ketone, and the like).

The optionally substituted alpha-olefin may be supplied to the hydroformylation zone in substantially pure form. Alternatively it may be admixed with one or more internal olefins. In mixtures containine one or more internal olefins the alpha-olefin is the major olefin component.

Besides the alpha-olefin(s), and possibly also internal olefin(s), hydrogen and carbon monoxide, there may be supplied to the hydroformylation one or more inert materials, such as inert gases (e.g. nitrogen, argon, carbon dioxide and gaseous hydrocarbons, such as methane, ethane, and propane). Such inert gases may be present in the alpha-olefin feedstock or in the synthesis gas. Other inert materials may include hydrogenation byproducts of the hydroformylation reaction, e.g. n-butane where the alpha-olefin is butene-1.

In many cases the process may be operated so that a part only of the make-up optionally substituted alpha-olefin, e.g. from about 15% to about 80% or higher, is converted in passage through the hydroformylation zone. Although the process can be operated on a "once through" basis, with unreacted alpha-olefin being exported beyond battery limits, possibly for other uses, after product recovery, it will usually be desirable to recycle unreacted alpha-olefin, after product recovery, to the hydroformylation zone. As some isomerisation of alpha-olefin to the corresponding internal olefin may occur in passage through the hydroformylation zone (e.g. in the case of butene-1 some isomerisation to butene-2 may occur), the recycle olefin stream may contain a minor amount, typically about 10% or less, of internal olefin, even though the alpha-olefin feedstock is substantially free from internal olefin. In addition it may contain byproduct hydrogenated feedstock. The concentration of internal olefin and of inert materials in the recycle stream or streams can be controlled in the usual way by taking purge streams at appropriate controlled rates.

It is also within the scope of the invention to utilise mixed feedstocks containing both alpha-olefin and internal olefin components. For example, it is possible to use a mixed $C_4$ hydrocarbon feedstock containing, in addition to butene-1, (and possibly also iso-butylene), also cis- and trans-butene-2, n-butane, iso-butane, and minor amounts of $C_{1-5}$ alkanes. In this case the internal olefins cis- and trans-butene-2 will be converted to the corresponding aldehyde, i.e. mainly 2-methylbutyraldehyde. In such mixed hydrocarbon feedstocks the major olefin component is the alpha-olefin, e.g. butene-1.

The organic phosphite ligand is preferably an at least bicyclic compound which contains a phosphorus atom in a bridgehead position linked to three oxygen atoms, each forming part of a cyclic system. Such ligands can be represented by the general formula:

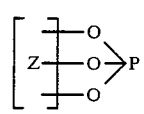
(I)

in which Z represents a trivalent organic group. In formula (I) Z may be acyclic or may comprise a cyclic group; in the former case the ligand of formula (I) is a bicyclic organic phosphite, whilst in the latter case the ligand of formula (I) is a tri- or poly-cyclic organic phosphite. As an example of a ligand of formula (I) in which Z comprises a cyclic group there can be mentioned the compound 2,8,9-trioxa-1-phosphatricyclo-[3.3.1.1^{3,7}]-decane of the formula:

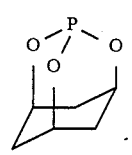
(II)

Other preferred organic bicyclic phosphite ligands are those of the general formula:

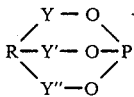　(III)

in which Y, Y' and Y'' each, independently of the others, represent a divalent organic radical, and R is a trivalent atom or group. Such compounds can be prepared by the methods described in the literature, for example, by transesterification of an organic phosphite of the general formula:

(R'O)$_3$P　(IV), in which each R' is an optionally substituted alkyl or aryl radical, such as methyl, ethyl, phenyl, benzyl, o-tolyl, naphthyl, hydroxymethyl or hydroxyethyl with a triol or higher polyol of the general formula:

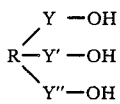　(V)

in which R, Y, Y' and Y'' are as defined above. One method of effecting transesterification comprises boiling the phosphite of formula (IV), e.g. triethyl phosphite, under reflux with a triol (or higher polyol) of formula (V), such as trimethylolpropane, optionally in the presence of a transesterification catalyst, e.g. sodium methoxide or triethylamine, and distilling off the alcohol of formula R'OH, e.g. ethanol, as it is formed.

Alternatively the cyclic organic phosphite ligand may be a monocyclic phosphite of the general formula:

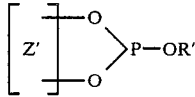　(VI)

in which Z' represents a divalent cyclic or acyclic radical and R' is as defined above. Preferred monocyclic ligands are those of the general formula:

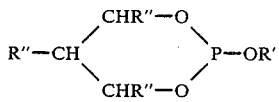　(VII)

in which R'' represents a hydrogen atom or one of the meanings of R' (defined above). The compounds of general formula (VI) can be made by methods known in the art for example by transesterification of an organic phosphite of formula (IV) with a diol of formula:

　(VIII)

in which Z' is as defined above.

In such a transesterification reaction the phosphite of formula (IV), e.g. trimethyl phosphite, triethyl phosphite, or triphenyl phosphite, may be heated under reflux with the diol of formula (VIII), optionally in the presence of a transesterification catalyst. Typical diols of formula (VIII) include 1,3-diols such as propane-1,3-diol and 2,2-dimethylpropane-1,3-diol, and hydrogenation products of alcohols and aldehyde condensation products such as "dimer (V)" of British Patent Specification No. 1338237.

As an example of a ligand of formula (VI) there can be mentioned 1-phenoxy-4,4-dimethyl-2,6-dioxa-1-phosphacyclohexane (2,2-dimethyl-propane-1,3-diol phenyl phosphite).

Particularly preferred cyclic phosphite ligands are those in which the bridgehead phosphorus atom forms part of one or more 6-membered rings.

In one preferred mode of operation the cyclic phosphite ligand is introduced as such into the hydroformylation reaction medium. Alternatively the ligand can be formed in situ by charging to the hydroformylation reaction medium a phosphite of a monohydric alcohol or phenol, e.g. trimethyl phosphite, triethyl phosphite, triphenyl phosphite, trinaphthyl phosphite, tri-n-butyl phosphite, tri-n-hexyl phosphite, or the like, and an at least equimolar quantity of an appropriate diol or of a polyol containing three or more hydroxyl groups, such as trimethylol propane or 1,3,5-trihydroxycyclohexane. Transesterification of the phosphite ester with the diol or polyol can be effected by heating the reaction medium, either before or after addition of the rhodium catalyst precursor, and either before or after commencement of hydroformylation.

In formula (III) R may represent, for example

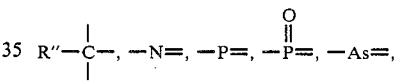

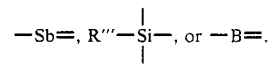

in which R'' is as defined above, and R''' is alkyl or alkoxy, e.g. methyl or methoxy. As examples of divalent organic radicals for which Y, Y' and Y'' may stand there may be mentioned alkylene, oxy-alkylene, alkylene-oxy-alkylene, alkylene-NR''''-alkylene, arylene, oxyarylene, alkylene-arylene, arylene-alkylene, alkylene-oxy-arylene, and arylene-oxy-alkylene; in such groups alkylene may be, for example, methylene, ethylene or ethylidene and arylene may be, for example, o-phenylene or m-phenylene, whilst R'''' represents an optionally substituted hydrocarbon radical, such as an alkyl radical. Preferably Y, Y' and Y'' contain no more than about 20 atoms in the chain.

Particularly preferred ligands are those of formula (III) in which Y, Y' and Y'' are methylene groups or substituted methylene groups, such as ethylidene groups. As examples of ligands of formula (III) there can be mentioned:
2,6,7-trioxa-1-phosphabicyclo-[2,2,2]-octane;
4-methyl-2,6,7-trioxa-1-phosphabicyclo-[2,2,2]-octane;
4-ethyl-2,6,7-trioxa-1-phosphabicyclo-[2,2,2]-octane;
4-hydroxymethyl-2,6,7-trioxa-1-phosphabicyclo-[2,2,2]-octane;
4-ethoxymethyl-2,6,7-trioxa-1-phosphabicyclo-[2,2,2]-octane;

4-acetoxymethyl-2,6,7-trioxa-1-phosphabicyclo-[2,2,2]-octane;
2,6,7-trioxa-1,4-diphosphabicyclo-[2,2,2]-octane;
4-iso-propyl-2,6,7-trioxa-1-phosphabicyclo-[2,2,2]-octane;
4-iso-propyl-3-methyl-2,6,7-trioxa-1-phosphabicyclo-[2,2,2]-octane;
4-n-butyl-2,6,7-trioxa-1-phosphabicyclo-[2,2,2]-octane;
4-n-hexyl-2,6,7-trioxa-1-phosphabicyclo-[2,2,2]-octane;
4-(2-ethylhexyl)-2,6,7-trioxa-1-phosphabicyclo-[2,2,2]-octane;
4-n-decyl-2,6,7-trioxa-1-phosphabicyclo-[2,2,2]-octane;
4-n-undecyl-2,6,7-trioxa-1-phosphabicyclo-[2,2,2]-octane;
3,5,8-trimethyl-2,6,7-trioxa-1-phosphabicyclo-[2,2,2]-octane;
3,4,5,8-tetramethyl-2,6,7-trioxa-1-phosphabicyclo-[2,2,2]-octane;
4-phenyl-2,6,7-trioxa-1-phosphabicyclo-[2,2,2]-octane;
4-cyclohexyl-2,6,7-trioxa-1-phosphabicyclo-[2,2,2]-octane;
4-capryloyloxymethyl-2,6,7-trioxa-1-phosphabicyclo-[2,2,2]-octane;
4-stearoyloxymethyl-2,6,7-trioxa-1-phosphabicyclo-[2,2,2]-octane;
3,5,8-trimethyl-4-phenyl-2,6,7-trioxa-1-phosphabicyclo-[2,2,2]-octane;
4-benzyl-2,6,7-trioxa-1-phosphabicyclo-[2,2,2]-octane;
3,4-dimethyl-2,6,7-trioxa-1-phosphabicyclo-[2,2,2]-octane; and the like.

The rhodium complex catalyst is dissolved in a liquid reaction medium in the process of the invention. This reaction medium comprises, in addition to the catalytic species, product aldehyde(s), aldehyde condensation products, alpha-olefin, hydrogenation product(s) derived from the alpha-olefin, and preferably also excess cyclic phosphite ligand. The nature of the aldehyde condensation products, and possible mechanisms for their formation during the course of the hydroformylation reaction, is explained in more detail in British Patent Specification No. 1,338,237, to which reference should be made for further information. Additionally the reaction medium may comprise an added inert solvent, such as benzene, toluene, acetone, methyl isobutyl ketone, t-butanol, n-butanol, tetralin, decalin, ethyl benzoate and the like. Usually, however, it will be preferred to operate in a "natural process solvent", i.e. a mixture of olefinically unsaturated compound, hydrogenation product(s) thereof, aldehyde product(s) and aldehyde condensation products. However, when operating continuously it may be preferred to use at start up an inert solvent, such as acetone, benzene, toluene, or the like, and then gradually to allow this to be displaced by "natural process solvent" by differential evaporation as the reaction progresses.

The rhodium concentration in the liquid reaction medium may vary from about 10 ppm or less up to about 1000 ppm or more, calculated in each case as rhodium metal and on a weight/volume basis. Typically the rhodium concentration in the liquid reaction medium lies in the range of from about 40 ppm up to about 200 ppm, calculated as rhodium metal. For economic reasons it will not usually be desirable to exceed about 500 ppm rhodium, calculated as metal, in the liquid reaction medium.

In the liquid reaction medium the cyclic phosphite ligand:Rh molar ratio is desirably at least about 1:1. Preferably the ligand:Rh molar ratio is from about 3:1 or 4:1 up to about 20:1 or more. The upper limit of concentration of cyclic phosphite ligand in the reaction medium will usually be about 10% w/v or the solubility limit of the cyclic phosphite ligand therein, whichever is the lower figure. Usually, however, it will be preferred to operate at cyclic phosphite ligand concentrations of less than about 1% w/v and phosphite ligand:Rh molar ratios of from about 5:1 up to about 16:1, e.g. about 8:1. Good results can often be obtained at concentrations of 0.5% w/v or less, e.g. 0.25% w/v or less, of cyclic phosphite ligand.

At least some of the cyclic phosphite ligands used in the process of the invention are highly toxic; extreme care should therefore be taken in handling the phosphite ligands and reaction media containing them.

The hydroformylation conditions utilised in the process of the present invention involve use of elevated temperatures e.g. in the range of from about 40° C. up to about 160° C. or more. Usually, however, it will be preferred to operate at as low a temperature as is possible, consistent with achieving a satisfactory reaction rate, so as to minimise the risk of isomerisation of the alpha-olefin to a corresponding internal olefin. Hence preferred operating temperatures usually range from about 70° C. up to about 130° C.; such temperatures are usually adequate for alpha-olefins containing the group —CH=CH$_2$. The reaction rate depends inter alia on the ligand:Rh molar ratio. Hence it will usually be necessary to increase the operating temperature, if the ligand:Rh molar ratio is increased beyond about 8:1, in order to maintain a substantially constant aldehyde productivity. When using ligand:Rh ratios of from about 3:1 to about 8:1, temperatures of about 70° C. to about 100° C. are usually suitable for alpha-olefins containing the group —CH=CH$_2$; higher temperatures, e.g. up to about 130° C., may be desirable if higher ligand:Rh molar ratios, e.g. about 12:1 or more, are used. Higher temperatures may, however, be necessary where the olefinic carbon-carbon bond is more hindered, as for example when the olefin contains the group >C=CH$_2$ (the free valencies indicated in the formula for this radical are in each case attached to an organic radical); for example, temperatures up to about 150° C. or higher may be necessary in this case in order to achieve satisfactory reaction rates. Use of such higher operating temperature will usually be accompanied by use of higher ligand:Rh molar ratios, e.g. about 8:1 or higher.

Elevated pressures are also typically used in the hydroformylation zone. Typically the hydroformylation reaction is conducted at a total pressure of from about 4 bar upwards up to about 75 bar or more. Usually it will be preferred to operate at a total pressure of not more than about 35 bar.

In the hydroformylation reaction 1 mole of carbon monoxide and 1 mole of hydrogen react with each alpha-olefinic bond. Thus, for example, in the case of butene-1, the major product is n-valeraldehyde which is formed by the reaction:

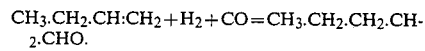

The isomeric aldehyde, 2-methylbutyaldehyde, is typically also formed as minor product as follows:

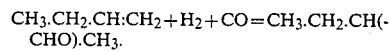

In addition some of the alpha-olefins may undergo hydrogenation; hence n-butane may be a byproduct when butene-1 is hydroformylated. Typically less than 5% of the alpha-olefin undergoes hydrogenation.

In operating the process of the invention in a continuous manner it is desirable to supply make up amounts of hydrogen and carbon monoxide in an approximately 1:1 molar ratio, e.g. about a 1.05:1 molar ratio. The formation of such mixtures of hydrogen and carbon monoxide can be effected by any of the methods known in the art for producing synthesis gas for hydroformylation, e.g. by partial oxidation of a suitable hydrocarbon feedstock such as natural gas, naphtha, fuel oil or coal.

In operating the process of the invention the total pressure of hydrogen and carbon monoxide in the hydroformylation zone can range from about 1.5 bar or less up to about 75 bar or more. The partial pressure of hydrogen may exceed that of carbon monoxide, or vice versa. For example the ratio of the partial pressures of hydrogen and of carbon monoxide may range from about 10:1 to about 1:10. At all events it will usually be desirable to operate at a partial pressure of hydrogen of at least about 0.05 bar up to about 30 bar and at a partial pressure of carbon monoxide of at least about 0.05 bar up to about 30 bar.

Product recovery can be effected in any convenient manner. In some instances, for example when using butene-1 as the olefinically unsaturated compound, it is possible to utilise a gas recycle process similar to that described in British Patent Specification No. 1582010. More usually, however, it will be more convenient to withdraw a portion of the liquid reaction medium from the hydroformylation zone either continuously or intermittently and to distil this in one or more stages under normal, reduced or elevated pressure, as appropriate, in a separate distillation zone in order to recover the aldehyde product(s) and other volatile materials in vaporous form, the rhodium-containing liquid residue being recycled to the hydroformylation zone. Condensation of the volatile materials and separation thereof, e.g. by distillation, can be carried out in conventional manner. Aldehyde product(s) can be passed on for further purification, whilst a stream containing unreacted alpha-olefin can be recycled to the hydroformylation zone together with any hydrogen and carbon monoxide that was dissolved in the reaction medium. A bleed stream can be taken from the recycle stream or streams in order to control build up of inerts (e.g. $N_2$) and of hydrogenation product(s) in the recycle streams.

The rhodium may be introduced into the reaction zone in any convenient manner. For example, the rhodium salt of an organic acid, such as rhodium acetate, i.e. $[Rh(OCOCH_3)_2.H_2O]_2$, can be combined with the ligand in the liquid phase and then treated with a mixture of carbon monoxide and hydrogen, prior to introduction of the alpha-olefin. Alternatively the catalyst can be prepared from a carbon monoxide complex of rhodium, such as dirhodium octacarbonyl, by heating with the cyclic phosphite ligand which thereby replaces one or more of the carbon monoxide molecules. It is also possible to start with the ligand of choice and finely divided rhodium metal, or with an oxide of rhodium (e.g. $Rh_2O_3$ or $Rh_2O_3.H_2O$) and the ligand, or with a rhodium salt of an inorganic acid, such as rhodium nitrate (i.e. $Rh(NO_3)_3.2H_2O$) and the ligand, and to prepare the active species in situ during the course of the hydroformylation reaction. Yet again it is possible to introduce into the reaction zone, as a catalyst precursor, a rhodium complex such as (pentane-2,4-dionato) dicarbonyl rhodium (I) which is then converted, under the hydroformylation conditions and in the presence of excess ligand, to the operative species. Other suitable catalyst precursors include $Rh_4(CO)_{12}$ and $Rh_6(CO)_{16}$.

When using polymeric aldehyde condensation products as solvent, the ratio of aldehyde to such products in the liquid reaction mixture in the hydroformylation zone may vary within wide limits. Typically this ratio lies in the range of from about 1:4 to about 4:1 by weight, e.g. about 1:1 by weight.

Under appropriate conditions aldehyde productivities in excess of about 0.5 g. moles/liter/hr can be achieved in the process of the invention. Hence it is usually preferred to supply make up alpha-olefin to the hydroformylation zone at a rate which corresponds to the aldehyde productivity of the system under the hydroformylation conditions selected. As the conversion per pass will usually be less than 100%, typically about 15% to about 80% or higher, it will be necessary to increase correspondingly the feed rate of the make up olefin if the process is to operate on a "once through" basis or to recycle unreacted olefin at an appropriate rate if the process operates with olefin recycle. Often the aldehyde productivity rate exceeds about 1.0 g. mole/liter/hr, e.g. up to at least about 2.5 g. moles/liter/hr or higher and the rate of supply of make up alpha-olefin must then equal or exceed this value.

In the course of our experiments we have found that, when using triphenylphosphine as ligand in a rhodium-catalysed hydroformylation system, it is some times necessary to raise the reaction temperature to about 120° C. in order to get commercially acceptable rates of hydroformylation. At this temperature, however, significant amounts of olefin may be isomerised to with the result that significant amounts of isomeric aldehydes are produced instead of the desired aldehyde. In addition the catalyst loses its activity over a period of time and the reaction solution changes colour from a clear yellow to a muddy brown solution which has little or no catalytic activity. Although the mechanism of deactivation is not entirely clear it is believed that rhodium clusters having phosphido bridges of the type:

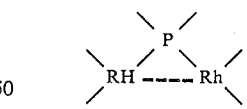

may be formed under certain conditions, this occurring by way of loss of one or more phenyl groups from the triphenylphosphine molecule. (In this formula the free valencies of the rhodium atoms may be attached to at least one other rhodium atom, whilst each of the free valencies on the phosphorus atom is attached either to an organic group, such as phenyl, or to a further rhodium atom). When triphenylphosphine is replaced by triphenylphosphite reaction commences at lower temperatures, e.g. about 70° C., but catalytic activity also declines fairly rapidly. Analysis of the reaction medium shows that triphenylphosphite is disappearing from the medium as the reaction proceeds. The at least bicyclic phosphite ligands that are preferably used in the process of the invention, on the other hand, although sharing with triphenylphosphite the great advantage of enabling lower reaction temperatures, of the order of 70° C., to be used, have the additional surprising advantage that they appear to be stable in the reaction medium, even at elevated temperatures, such as about 120° C. or higher. It has also been observed that, when using an at least bicyclic phosphite ligand, triphenylphosphine appeared to act under certain conditions as a catalyst deactivator.

The invention is illustrated further in the following Examples.

EXAMPLE 1

The continuous hydroformylation of butene-1 was investigated using a stainless steel reactor of nominal capacity 300 ml which is fitted with a magnetically coupled stirrer and with an internal cooling coil through which air could be blown for temperature control purposes. The reactor was also fitted with a gas inlet tube for admission of a $CO/H_2$ mixture to the gas space and an inlet tube for liquid butene-1, each in the form of a dip tube ending near the bottom of the reactor, as well as with a liquid outlet tube in the form of a dip tube whose open lower end was positioned at a level corresponding to the surface level of a volume of 150 ml of liquid in the reactor. Butene-1 was charged to a feed vessel which was pressurised to 4.5 kg/cm² absolute (446 kPa) with $O_2$-free nitrogen and which was connected to the corresponding inlet tube of the reactor by way of a feed pump and a non-return valve. Carbon monoxide and hydrogen were supplied from individual cylinders thereof through individual pressure controllers and then by way of a two channel mass flow controller through an oxygen guard unit (to ensure that the synthesis gas fed to the reactor was oxygen-free).

Liquid in excess of 150 ml together with unreacted gases exited the reactor through the outlet tube and passed through a cooler to a gas-liquid separator which acted as a knock out pot. The gas from the knock out pot was passed through a letdown valve which let its pressure down to atmospheric pressure and was then supplied to a wet gas meter and vented. The separated reactor solution in the knock out pot was maintained at a specific volume using a level controller which let down excess liquid through a capillary tube to a product evaporator consisting of a Liebig condenser packed with Ballotini glass beads. The majority of the liquid passed through the beads and fell into a receiver which was also fitted with a level controller. When this level controller indicated that the liquid in the receiver exceeded a preselected volume hot oil was pumped through the evaporator. The stripped reactor solution was pumped back from the receiver to the reactor at a constant rate by means of a catalyst recycle pump.

The flashed butene-1 and product passed overhead through a cooler to the product receiver, where the majority of the product was collected. Some of the unreacted butene-1 was dissolved in the product condensate, whilst the remainder passed on through a meter.

The reactor was heated by immersion in a thermostatically controlled oil bath, fine temperature control being exerted automatically by blowing air on demand through the internal cooling coil. The level controllers were set so that the total liquid inventory of the catalyst containing solution was 200 ml, i.e. an inventory of 50 ml outside the reactor.

To monitor the course of the reaction the gas flow rates were measured and gas chromatographic analyses were performed by sampling the system as follows:

| Sample stream | Components |
|---|---|
| Inlet synthesis gas | $H_2$, CO |
| Exit gas from knock out pot | $H_2$, CO, aldehydes, butenes, butane |
| Butene off gas | $H_2$, CO, butenes, butane, aldehydes |
| Product | Aldehydes, aldehyde by-products, butenes, butane |
| Reactor solution | Aldehydes, aldehyde by-products, butenes, butane, ligand concentration |

$H_2$ and CO were determined using a 1.85 m×4.76 mm o.d. stainless steel column packed with molecular sieve (5 Å) at 110° C. Butenes and butane were determined using a 1.85 m×4.76 mm o.d. stainless steel column packed with Porasil C at 60° C. Aldehydes and aldehyde byproducts were determined using a 1.85 m×4.76 mm o.d. stainless steel column packed with 10% OV 101 on Chromosorb PAW which was temperature programmed to run at 50° C. for 5 minutes and then to increase in temperature at 10° C./minute to 300° C. Ligand concentration was determined using a phosphorus specific flame photometric detector and a 0.46 m×4.76 mm o.d. stainless steel column packed with 10% OV 101 on Chromosorb PAW run at 220° C.

At start up the empty reactor was purged with nitrogen and then pressurised to 29.2 kg/cm² absolute (2863 kPa) with the $CO/H_2$ mixture and a flow of the hydrogen/carbon monoxide mixture in excess of the anticipated reaction demand was established through the system using the mass flow controllers. Then acetone was charged to the system via the sample point for the product evaporator bottoms using the catalyst recycle pump. When 100 ml of acetone had been charged the reactor stirrer was switched on and adjusted to run at 1500 r.p.m. Once automatic level control had been achieved addition of acetone was terminated. The feedstock pump was then switched on so as to give a butene-1 feed rate of 60 ml/hr and the system allowed to equilibriate under automatic control.

Next 0.1 g $[Rh(OCOCH_3)_2.H_2O]_2$ (equivalent to 0.418 millimoles of Rh) and 0.5 g (3.08 millimoles) TMPP, i.e. 4-ethyl-2,6,7-trioxa-1-phosphabicyclo-[2,2,2]-octane, were charged to the system via the evaporator bottoms sample point. This corresponds to a TMPP:Rh molar ratio of 7.4:1. When the system was homogeneous the reactor temperature was raised to 98.5° C. Onset of reaction was detected by a decrease in the effluent synthesis gas from the knock out pot, accompanied by more frequent operation of the oil pump to the product evaporator and by the appearance of liquid in the product receiver. As the reaction proceeded the acetone initially charged to the system was replaced within the system by product aldehydes.

The effluent synthesis gas flow rate from the knock out pot (measured at atmospheric pressure), its composition, and other data measured are set out in Table I below. The catalyst solution recycle rate was 270 ml/hr.

EXAMPLE 2

The same general procedure as used in Example 1 was used, except that iso-butene was used, in place of butene-1, at a liquid feed rate of 60 ml/hr. The reaction system was charged with 0.1 g $Rh(CO)_2(AcAc)$, where AcAc represents acetylactone, corresponding to 0.388 millimoles of Rh, and with 0.5 g TMPP, i.e. 4-ethyl-2,6,7-trioxa-1-phospha-bicyclo-[2,2,2]-octane corresponding to 3.08 millimoles of TMPP. The reactor temperature was 119.5° C. The effluent synthesis gas flow rate from the knock out pot was measured to be 32 l/hr (measured at atmospheric pressure). This analysed as 56% $H_2$, 44% CO. The operating pressure was 22.1 kg/cm² absolute (2173.5 kPa). The liquid recycle rate was 270 ml/hr. The observed aldehyde productivity was 1.38 g. mole/l./hr. corresponding to an iso-butene conversion of 31%. The product distribution was as follows:

| | |
|---|---|
| 3-methylbutyraldehyde | 98.0% |
| 2,2-dimethylpropionaldehyde | 0.6% |
| iso-butane | 1.4%. |

TABLE I

| Temp. (°C.) | ESR (l./hr) | ESC $H_2$ | ESC CO | AP (g mole/l/hr) | Product distribution (%) VAL | 2-MBAL | n-Butane | Butene-2 | Butene-1 conversion (%) |
|---|---|---|---|---|---|---|---|---|---|
| 78 | 26 | 86 | 14 | 1.24 | 76.6 | 21.9 | 1.0 | 0.5 | 28.4 |
| 90 | 18 | 90 | 10 | 2.47 | 77.4 | 18.6 | 2.0 | 2.0 | 57.8 |
| 95 | 18 | 99 | 1 | 2.76 | 72.9 | 16.1 | 6.0 | 5.0 | 67.3 |
| 101 | 18 | 99.5 | 0.5 | 2.76 | 68.9 | 10.1 | 14.0 | 7.0 | 73.7 |

Notes:
ESR = Effluent synthesis gas flow rate (measured at atmospheric pressure)
ESC = Effluent synthesis gas composition
AP = Aldehyde productivity

COMPARATIVE EXAMPLE A

Using the same general procedure as used in Example 1, except that in place of the rhodium acetate and TMPP there are used equivalent amounts of $HRh(CO)(PPh_3)_3$, and triphenylphosphine, it is observed that aldehyde productivity declines at a rate with time that would not be acceptable in a commercial plant.

COMPARATIVE EXAMPLE B

The procedure of Example 1 is repeated using equivalent amounts of $[Rh(OCOCH_3)_2.H_2O]_2$, and of triphenylphosphite. Over a period of about 48 hours the aldehyde productivity is observed to decline markedly and the level of free triphenylphosphite also declines significantly.

EXAMPLE 3

Using the general procedure of Example 1 propylene is hydroformylated to produce a mixture of n- and iso-butyraldehydes.

EXAMPLE 4

Using the general technique described in Example 1, the hydroformylation of butene-1 was studied under the following conditions:

| | |
|---|---|
| Temperature | 80° C. |
| Rhodium Concentration | 200 ppm |
| Ligand | 4-methyl-2,4,7-trioxa-1-phosphabicyclo-[2,2,2]-octane |
| Ligand Concentration | 0.25% w/v |
| Pressure | 22.15 kg/cm² absolute (2173.5 kPa) |
| Catalyst Solution Recycle Rate | 60 ml/hr |
| Butene-1 Feed Rate | 68 ml/hr liquid |

After 16 hours from start up the productivity was observed to be 1.59 g mol/l/hr aldehyde. The conversion per pass of butene-1 was 32.1%. The following selectivities were noted:
 less than 0.5% to n-butane
 71% to n-valeraldehyde
 29% to 2-methylbutyraldehyde

EXAMPLE 5

Following the general procedure of Example 1 the hydroformylation of butene-1 was investigated using as ligand 4-ethoxymethyl-2,6,7-trioxa-1-phosphabicyclo-[2,2,2]-octane. The conditions were as follows:

| | |
|---|---|
| Temperature | 70° C. |
| Rhodium Concentration | 200 ppm (charged in the form of 0.1 g acetylacetonatodicarbonyl rhodium (I)) |
| Ligand Concentration | 0.25% w/v |
| Pressure | 22.15 kg/cm₂ absolute (2173.5 kPa) |
| Catalyst Solution Recycle Rate | 60 ml/hr |
| Butene-1 Feed Rate | 68 ml/hr liquid |

After allowing the system to stabilise the reaction rate was measured to be 1.54 g mol/l/hr. The conversion of butene-1 per pass was 31%. Analysis of the products indicated selectivities to n-butane of less than 0.5%, to n-valeraldehyde of 71%, and to 2-methylbutyraldehyde of 28%.

EXAMPLE 6

The procedure of Example 5 was repeated using 4-acetoxymethyl-2,6,7-trioxa-1-phosphabicyclo-[2,2,2]-octane as ligand. The conditions used were as follows:

| | |
|---|---|
| Temperature | 75° C. |
| Rhodium Concentration | 200 ppm |
| Ligand Concentration | 0.25% w/v |
| Pressure | 22.15 kg/cm² (2173.5 kPa) |
| Catalyst Solution Recycle Rate | 60 ml/hr |
| Butene-1 Feed Rate | 68 ml/hr liquid |

After allowing the system to equilibrate for some hours the reaction rate was measured to be 1.36 g mol/l/hr. The conversion of butene-1 per pass was 28.4%. The following selectivites were noted:
 less than 0.5% to n-butane
 73% of n-valeraldehyde
 27% to 2-methylbutyraldehyde.

We claim:

1. A continuous process for the production of an aldehyde by hydroformylation of an alpha-olefin feedstock selected from the group consisting of alpha-olefins and substituted alpha-olefins which comprises:
providing a hydroformylation zone containing a charge of a liquid reaction medium having dissolved therein a complex rhodium hydroformylation catalyst comprising rhodium in complex combination with carbon monoxide and with a cyclic phosphite having a bridgehead phosphorus atom linked to three oxygen atoms at least two of which form together with the bridgehead phosphorus atom part of a ring;
continuously supplying said alpha-olefin feedstock to the hydroformylation zone;
maintaining in the hydroformylation zone a temperature in the range of from about 40° C. to about 160° C. and a pressure in the range of from about 4 bar to about 75 bar;
supplying make-up hydrogen and carbon monoxide to the hydroformylation zone; and
recovering from the liquid hydroformylation medium a hydroformylation product comprising at least one aldehyde.

2. A process according to claim 1, in which the cyclic phosphite is an at least bicyclic phosphite of the general formula:

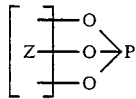  (I)

in which Z represents a trivalent cyclic or acylic organic group.

3. A process according to claim 2, in which the cyclic phosphite ligand is 2,8,9-trioxa-1-phosphatricyclo-[3.3.1.1$^{3,7}$]-decane.

4. A process according to claim 2, in which the cyclic phosphite ligand is selected from 4-methyl-2,6,7,-trioxa-1-phosphabicyclo-[2,2,2]-octane, 4-ethyl-2,6,7-trioxa-1-phosphabicyclo-[2,2,2]-octane, 4-ethoxymethyl-2,6,7-trioxa-1-phosphabicyclo-[2,2,2]-octane, and 4-acetoxymethyl-2,6,7-trioxa-1-phosphabicyclo-[2,2,2]-octane.

5. A process according to claim 1, in which the cyclic phosphite is a monocyclic phosphite of the general formula:

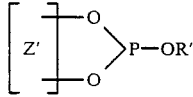  (VI)

in which Z' represents a divalent cyclic or acyclic organic radical and R' represents an optionally substituted alkyl or aryl radical.

6. A process according to claim 1, in which the alpha-olefin is butene-1 and the hydroformylation product comprises n-valeraldehyde.

7. A process according to claim 1, in which the alpha-olefin is iso-butene and the hydroformylation product comprises 3-methylbutyraldehyde.

8. A process according to claim 1, in which the alpha-olefin is supplied to the hydroformylation zone in admixture with a smaller molar amount of an internal olefinic compound.

9. A process according to claim 1, in which the hydroformylation zone is maintained at a temperature of from about 40° C. up to about 160° C., at a total pressure of from about 4 bar up to about 35 bar, at a partial pressure of hydrogen and of carbon monoxide each of at least about 0.05 bar, and at a ratio of partial pressures of hydrogen and of carbon monoxide in the range of from about 10:1 to about 1:10.

10. A process according to claim 1, in which the cyclic phosphite ligand:Rh molar ratio is at least about 3:1.

11. A process according to claim 1, in which recovery of the hydroformylation product includes withdrawal of reaction medium from the hydroformylation zone and distillation thereof in one or more stages under normal, reduced or elevated pressure.

12. A process according to claim 11, in which the distillation step yields also a stream comprising unreacted alpha-olefin which is recycled to the hydroformylation zone.

13. A process according to claim 1, in which the reaction medium comprises aldehyde product and aldehyde condensation products as solvent.

14. A process according to claim 1, in which make-up alpha-olefin feedstock is continuously supplied to the hydroformylation zone at a rate corresponding to at least about 0.5 gram moles per liter of reaction medium per hour.

15. A process according to claim 1, in which the cyclic phosphite is formed in situ by transesterification of an organic phosphite of the general formula:

$(R'O)_3P$  (IV)

in which each R' is an optionally substituted alkyl or aryl radical with a triol or higher polyol of the general formula:

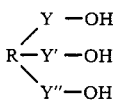  (V)

in which Y, Y' and Y" each, independently of the others, represent a divalent organic radical, and R is a trivalent atom or group, or with a diol of the general formula:

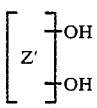  (VI)

in which Z' represents a divalent cyclic or acyclic radical.

* * * * *

UNITED STATES PATENT AND TRADEMARK OFFICE
CERTIFICATE OF CORRECTION

PATENT NO. : 4,496,768
DATED : 1/29/85
INVENTOR(S) : Alan James Dennis, George Edwin Harrison and
James Peter Wyber It is certified that error appears in the above-identified patent and that said Letters Patent is hereby corrected as shown below:

Cover page,

Under "Foreign Application Priority Data"
      change the date "Nov. 6, 1982" to
        --June 11, 1982--

Column 4, line 48, change "brightened" to
        --bridgehead--

Column 4, line 61, change "rhdoium" to
        --rhodium--

Column 5, line 59, change "containine" to
        --containing--

Column 17, line 37, change "acylic" to
        --acyclic--

Signed and Sealed this

Twelfth Day of August 1986

[SEAL]

Attest:

DONALD J. QUIGG

Attesting Officer      Commissioner of Patents and Trademarks